United States Patent [19]
Hawkins et al.

[11] Patent Number: 5,846,778
[45] Date of Patent: Dec. 8, 1998

[54] HUMAN MAP KINASE HOMOLOG

[75] Inventors: Phillip R. Hawkins, Mountain View; Janice Au-Young, Berkeley; Karl J. Guegler, Menlo park; Craig G. Wilde, Sunnyvale, all of Calif.

[73] Assignee: Incyte Pharmaceuticals, Inc., Palo Alto, Calif.

[21] Appl. No.: 920,296

[22] Filed: Aug. 28, 1997

Related U.S. Application Data

[62] Division of Ser. No. 674,612, Jun. 28, 1996, Pat. No. 5,663,313.

[60] Provisional application No. 60/000,722 Jun. 30, 1995.

[51] Int. Cl.⁶ .................... C12N 15/00; C07K 14/435; C07H 21/04
[52] U.S. Cl. .................. 435/69.1; 435/320.1; 536/23.5; 530/350; 530/827; 935/9; 935/11
[58] Field of Search ............................ 435/69.1, 320.1; 536/23.5; 530/350, 827; 935/9, 11

[56] References Cited

FOREIGN PATENT DOCUMENTS

WO A9423039   10/1994   WIPO .

OTHER PUBLICATIONS

Davis, RJ, "MAPKs: new JNK expands the group" *TIBS* 19:470–473 (1994).

Dérijard, et al., "Independent Human MAP Kinase Signal Transduction Pathways Defined by MEK and MKK Isoforms" *Science* 267:682–686 (1995).

Egan, SE and Weinberg, RA, "The pathway to signal achievement" *Nature* 365:781–783 (1993).

Han et al., "A MAP Kinase Targeted by Endotoxin and Hyperosmolarity in Mammalian Cells" *Science* 265:808–811 (1994).

Lee et al., "A protein kinase involved in the regulation of inflammatory cytokine biosynthesis" *Nature* 372:739–745 (1994).

*Primary Examiner*—Carla J. Myers
*Attorney, Agent, or Firm*—Lucy J. Billings; Sheela Mohan-Peterson

[57] ABSTRACT

The present invention provides nucleic acid and amino acid sequences that identify and encode a novel human map kinase homolog (SMAP) expressed in cells of the human stomach. The present invention also provides for PCR oligomers or hybridization probes for the detection of nucleotide sequences encoding SMAP or SMAP-like molecules, antisense molecules to the nucleotide sequences which encode SMAP, diagnostic tests based on SMAP encoding nucleic acid molecules, genetically engineered expression vectors and host cells for the production of purified SMAP, antibodies capable of binding specifically to SMAP, and agonists and inhibitors with specific binding activity for the polypeptide SMAP.

2 Claims, 5 Drawing Sheets

```
5' ATG AGC CTC ATC CGG AAA AAG GGC TTC TAC AAG CAG GAC GTC AAC AAG ACC GCC       54
    M   S   L   I   R   K   K   G   F   Y   K   Q   D   V   N   K   T   A

TGG GAG CTG CCC AAG ACC TAC GTG TCC CCG ACG CAC GTC GGC AGC GGG GCC TAT      108
     W   E   L   P   K   T   Y   V   S   P   T   H   V   G   S   G   A   Y

GGC TCC GTG TGC TCG GCC ATC GAC AAG CGG TCA GGG GAG AAG CGC ATC AAG          162
     G   S   V   C   S   A   I   D   K   R   S   G   E   K   V   A   I   K

AAG CTG AGC CGA CCC TTT CAG TCC ATC ATT CAT GCC AAG CGC ACC TAC CGG GAG      216
     K   L   S   R   P   F   Q   S   I   I   H   A   K   R   T   Y   R   E

CTG CTG AAG CTG CTG CGA TCC CAC ATG CAG AAC TTC ATC GGG CTC TTG GAT GTC      270
     L   L   K   L   L   R   S   H   M   Q   N   F   I   G   L   L   D   V

TTC ACC CCA GCC TCC TCC CTG NGN AAC TTC TAT GAC TTC TAC CTG GTG ATG CCC      324
     F   T   P   A   S   S   L   X   N   F   Y   D   F   Y   L   V   M   P

TTC ATG CAG ACG GAT CTG CAG AAG ATC ATG GGG ATG GAG TTC AGT GAG GAG AAG      378
     F   M   Q   T   D   L   Q   K   I   M   G   M   E   F   S   E   E   K
```

FIGURE 1A

```
ATC CAG TAC CTG GTG TAT CAG ATG CTC AAA GGC CTT AAG TAC ATC CAC TCT GCT
 I   Q   Y   L   V   Y   Q   M   L   K   G   L   K   Y   I   H   S   A
387         396         405         414         423         432

GGG GTC GTG CAC AGG GAC CTG AAG CCA GGC AAC CTG GCT GTG AAT GAG GAC TGT
 G   V   V   H   R   D   L   K   P   G   N   L   A   V   N   E   D   C
441         450         459         468         477         486

GAA CTG AAG ATT CTG GAT TTG GGG CTG GCG CGA CAT GCA GAC GCC GAG ATG ACT
 E   L   K   I   L   D   L   G   L   A   R   H   A   D   A   E   M   T
495         504         513         522         531         540

GGC TAC GTG GTG ACC CGC TGG TAC CGA GCC CCC GAG GTG ATC CTC AGC TGG ATG
 G   Y   V   V   T   R   W   Y   R   A   P   E   V   I   L   S   W   M
549         558         567         576         585         594

CAC TAC AAC CAG ACA GTG GAC ATC TGG TCT GTG GGC TGT ATC ATG GCA GAG ATG
 H   Y   N   Q   T   V   D   I   W   S   V   G   C   I   M   A   E   M
603         612         621         630         639         648

CTG ACA GGG AAA ACT CTG TTC AAG GGG AAA GAT TAC CTG GAC CAG CTG ACC CAG
 L   T   G   K   T   L   F   K   G   K   D   Y   L   D   Q   L   T   Q
657         666         675         684         693         702

ATC CTG AAA GTG ACC GGG GTG CCT GGC ACG GAG TTT GTG CAG AAG CTG AAC GAC
 I   L   K   V   T   G   V   P   G   T   E   F   V   Q   K   L   N   D
711         720         729         738         747         756
```

FIGURE 1B

```
AAA GCG GCC AAA TCC TAC ATC CAG TCC CTG CCA CAG ACC CCC AGG AAG GAT TTC
 K   A   A   K   S   Y   I   Q   S   L   P   Q   T   P   R   K   D   F
765             774         783         792         801         810

ACT CAG CTG TTC CCA CGG GCC AGC CCC CAG CCT GCG GAC CTG GAG AAG ATG
 T   Q   L   F   P   R   A   S   P   Q   P   A   D   L   E   K   M
819             828         837         846         855         864

CTG GAG CTA GAC AAG CGC CTG ACG GCC CAG GCC CTC ACC CAT CCC
 L   E   L   D   K   R   L   T   A   Q   A   L   T   H   P
873             882         891         900         909         918

TTC TTT GAA CCC TTC CGG GAC CCT GAG GAA GAG ACG GCC CAG CAG CCG TTT
 F   F   E   P   F   R   D   P   E   E   E   T   A   Q   Q   P   F
927             936         945         954         963         972

GAT GAT TCC TTA GAA CAC GAG AAA CTC ACA GTG GAT GAA TGG AAG CAC ATC
 D   D   S   L   E   H   E   K   L   T   V   D   E   W   K   H   I
981             990         999         1008        1017        1026

TAC AAG GAG ATT GTG AAC TTC AGC CCC ATT GCC CGG AAG GAC TCA CGG CGC CGG
 Y   K   E   I   V   N   F   S   P   I   A   R   K   D   S   R   R   R
1035            1044        1053        1062        1071        1080

AGT GGC ATG AAG CTG TAG 3'
 S   G   M   K   L   *
1089            1098
```

FIGURE 1C

```
  1   M S L I R K K G F Y K Q D V N K T A W E L P K T Y V S P T H V G S G A Y G S V C    SMAP
  1   M S Q E R P T - F Y R Q E L N K T I W E V P E R Y Q N L S P V G S G A Y G S V C    MMU10871

41   S A I D K R S G E K V A I K K L S R P F Q S E I F A K R A Y R E L L L L K H M Q    SMAP
 40   A A F D T K T G H R V A V K K L S R P F Q S I I H A K R T Y R E L R L L K H M K    MMU10871

81   H E N V I G L L D V F T P A S S L X N F Y D F Y L V M P F M Q T D L Q K I M G -    SMAP
 80   H E N V I G L L D V F T P A R S L E E F N D V Y L V T H L M G A D L N N I V K C    MMU10871

120   M E F S E E K I Q Y L V Y Q M L K G L K Y I H S A G V V H R D L K P G N L A V N    SMAP
120   Q K L T D D H V Q F L I Y Q I L R G L K Y I H S A D I I H R D L K P S N L A V N    MMU10871

160   E D C E L K I L D L G L A R H A D A E M T G Y V V T R W Y R A P E V I L S W M H    SMAP
160   E D C E L K I L D F G L A R H T D D E M T G Y V V A T R W Y R A P E I M L N W M H    MMU10871

200   Y N Q T V D I W S V G C I M A E M L T G K T L F K G K D Y L D Q L T Q I L K V T    SMAP
200   Y N Q T V D I W S V G C I M A E L L T G R T L F P G T D H I D Q L K L I L R L V    MMU10871

240   G V P G T E F F V Q K L N D K A A K S Y I Q S L P Q T P R K D F T Q L F P R A S P    SMAP
240   G T P G A E L L K K I S S E S A R N Y I Q S L A Q M P K M N F A N V F I G A N P    MMU10871

280   Q P A D L L E K M L E L D V D K R L T A A Q A L T H P F F E P F R D P E E E T E    SMAP
280   L A V D L L E K M L V L D S D K R I T A A Q A L A H A Y E A Q Y H D P D D E P -    MMU10871

320   A Q Q P F D D S L E H E K L T V D E W K Q H I Y K E I V N F S P I A R K D S R R    SMAP
319   V A D P Y D Q S F E S R D L L I D E W K S L T Y D E V I S F V P P P L D Q E - -    MMU10871

360   R S G M K L                                                                       SMAP
357   - - E M E S                                                                       MMU10871
```

FIGURE 2

```
  1  M S L I R K K G F Y K Q D V N K T A W E L P K T Y V S P T H V G S G A Y G S V C   SMAP
  1  M S Q E R P T - F Y R Q E L N K T I W E V P E R Y Q N L S P V G S G A Y G S V C   HUMCSBP1

41  S A I D K R S G E K V A I K K L S R P F Q S E I F A K R A Y R E L L L K H M Q     SMAP
 40  A A F D T K T G L R V A V K K L S R P F Q S I I H A K R T Y R E L R L L K H M K   HUMCSBP1

81  H E N V I G L L D V F T P A S S L X N F Y D F Y L V M P F M Q T D L Q K I M G -   SMAP
 80  H E N V I G L L D V F T P A R S L E E F N D V Y L V T H L M G A D L N N I V K C   HUMCSBP1

120  M E F S E E K I Q Y L V Y Q M L K G L K Y I H S A G V V H R D L K P G N L A V N   SMAP
120  Q K L T D D H V Q F L I Y Q I L R G L K Y I H S A D I I H R D L K P S N L A V N   HUMCSBP1

160  E D C E L K I L D L G L A R H A D A E M T G Y V V T R W Y R A P E V I L S W M H   SMAP
160  E D C E L K I L D F G L A R H T D D E M T G Y V V A T R W Y R A P E I M L N W M H HUMCSBP1

200  Y N Q T V D I W S V G C I M A E M L T G K T L F K G K D Y L D Q L T Q I L K V T   SMAP
200  Y N Q T V D I W S V G C I M A E L L T G R T L F P G T D H I N Q L Q Q I M R L T   HUMCSBP1

240  G V P G T E F V Q K L N D K A A K S Y I Q S L P Q T P R K D F T Q L F P R A S P   SMAP
240  G T P P A Y L I N R M P S H E A R N Y I Q S L T Q M P K M N F A N V F I G A N P   HUMCSBP1

280  Q P A D L L E K M L E L D V D K R L T A A Q A L T H P F F E F R D P E E E T E     SMAP
280  L A V D L L E K M L V L D S D K R I T A A Q A L A H A Y F A Q Y H D P D D E P -   HUMCSBP1

320  A Q Q P F D D S L E H E K L T V D E W K Q H I Y K E I V N F S P I A R K D S R R   SMAP
319  V A D P Y D Q S F E S R D L L I D E W K S L T Y D E V I S F V P P P L D Q E - -   HUMCSBP1

360  R S G M K L                                                                       SMAP
357  - - E M E S                                                                       HUMCSBP1
```

FIGURE 3

HUMAN MAP KINASE HOMOLOG

This application is a divisional application of application Ser. No. 08/674,612, filed Jun. 28, 1996, now U.S. Pat. No. 5,663,313, which claims the benefit of U.S. Provisional application Ser. No. 60/000,722, filed Jun. 30, 1995.

TECHNICAL FIELD

The present invention is in the field of molecular biology; more particularly, the present invention describes a nucleic acid sequence and an amino acid sequence for a novel human MAP kinase homolog.

BACKGROUND ART

Mitogen-Activated Protein (MAP) Kinases

Mitogen-activated protein (MAP) kinases are a family of enzymes which regulate intracellular signaling pathways. MAP kinases are important mediators of signal transduction from cell surfaces to nuclei via phosphorylation cascades. Several subgroups of MAP kinases have been defined and each manifests different substrate specificities and responds to various distinct extracellular stimuli. Thus, the MAP kinase signaling pathways represent common mechanisms for signal transduction by which different extracellular stimuli generate distinct physiological responses inside cells (Egan, S. E. and Weinberg, R. A. (1993) Nature 365: 781–783).

Various MAP kinase signaling pathways have been defined in mammalian cells as well as in yeast. In mammalian cells, the extracellular stimuli activating the MAP kinase signaling pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). In the yeast, *Saccharomyces cerevisiae*, various MAP kinase signaling pathways are activated by exposure to mating pheromone or hyperosmolar environments and during cell-wall construction, sporulation and mitosis.

There are at least three subgroups of MAP kinases in mammalian cells (Derijard, B. et al (1995) Science 267: 682–5), and each subgroup is distinguished by a tripeptide sequence motif. They are extracellular signal-regulated protein kinase (ERK) characterized by Thr-Glu-Tyr, c-Jun amino-terminal kinase (JNK) characterized by Thr-Pro-Tyr, and p38 kinase characterized by Thr-Gly-Tyr. The subgroups are activated by the dual phosphorylation of the threonine and tyrosine by MAP kinase kinases located upstream of the phosphorylation cascade. Activated MAP kinases phosphorylate other effectors downstream ultimately leading to changes inside the cell.

MAP Kinase Subgroup ERK

The ERK signal transduction pathway is activated via tyrosine kinase receptors on the plasma membrane of the cell. When EGF or other growth factors bind to the tyrosine receptors, they, in turn, bind to noncatalytic, src homology (SH) adaptor proteins (SH2-SH3-SH2) and a guanine nucleotide releasing protein. The latter reduces GTP and activates Ras proteins, members of the large family of guanine nucleotide binding proteins (G-proteins). The activated Ras proteins bind to a protein kinase C-Raf-1 and activate the Raf-1 proteins. The activated Raf-1 kinase subsequently phosphorylates MAP kinase kinases which, in turn, activate MAP kinase ERKs by phosphorylating the threonine and tyrosine residues of the ERKs.

ERKs are proline-directed protein kinases which phosphorylate Ser/Thr-Pro motifs. In fact, cytoplasmic phospholipase A2 (cPLA2) and transcription factor Elk-1 are substrates of the ERKs. The ERKs phosphorylate $Ser_{505}$ of cPLA2 and cause an increase in its enzymatic activity resulting in an increased release of arachidonic acid and the formation of lysophospholipids from membrane phospholipids. Likewise, phosphorylation of the transcription factor Elk-1 by ELK ultimately results in increased transcriptional activity.

MAP Kinase Subgroup JNK

An analysis of a deduced primary sequence of the two isoforms of JNK, 46 kDa and 55 kDa, reveals that they are distantly related to the ELK subgroup. They are similarly activated by dual phosphorylation of Thr and Tyr, and the MKK4, MAP kinase kinases (Davis, R. (1994) TIBS 19: 470–473). The JNK signal transduction pathway can also be initiated by ultraviolet light, osmotic stress, and the pro-inflammatory cytokines, TNF and IL-1. The Ras proteins may partially activate the JNK signal transduction pathway. JNKs phosphorylate $Ser_{63}$ and $Ser_{73}$ in the amino-terminal domain of the transcription factor c-Jun which results in increased transcriptional activity.

MAP Kinase Subgroup p38

An analysis of the cDNA sequence encoding p38 shows that p38 is a 41 kD protein containing 360 amino acids. Its dual phosphorylation is activated by the MAP kinase kinases, MKK3 and MKK4. The p38 signal transduction pathway is also activated by heat shock, hyperosmolar medium, IL-1 or LPS endotoxin (Han, J. et al (1994) Science 265: 808–811) produced by invading gram-negative bacteria. The human body reacts to the invading bacteria by activating cells in the immune and inflammatory systems to initiating the systemic response called sepsis. Sepsis is characterized by fever, chills, tachypnea, and tachycardia, and severe cases may result in septic shock which includes hypotension and multiple organ failure.

LPS may be thought of as a stress signal to the cell because it alters normal cellular processes by inducing the release of mediators such as TNF which has systemic effects. CD14 is a glycosylphosphatidyl-inositol-anchored membrane glycoprotein which serves as an LPS receptor on the plasma membrane of cells of monocytic origin. The binding of LPS to CD14 causes rapid protein tyrosine phosphorylation of the 44- and 42- or 40-kD isoforms of MAP kinases. Although they bind LPS, these MAP kinase isoforms do not appear to belong to the p38 subgroup.

Other MAP Kinase Homologs

Recent research (Lee, J. C. et al (1994) Nature 372: 739–745) has revealed that a new series of pyridinyl-imidazole compounds, which inhibit LPS-mediated human monocyte IL-1 and TNF-α production actually work through a pair of closely related MAP kinase homologs, termed cytokine suppressive binding proteins (CSBPs). These compounds are cytokine-suppressive anti-inflammatory drugs (CSAIDs) which prevent phosphorylation and subsequent cytokine biosynthesis. A comparison of fragments of CSBP sequences with those of MAP kinases shows that genes encoding CSBPs are novel although related to protein serine/threonine kinases. It appears that CSBP proteins may be critical for cytokine production during human immune or inflammatory reactions.

Understanding the mechanism for blocking the specific kinase activities may provide a new way of treating inflammatory illnesses. Likewise, a thorough understanding of the various MAP kinase signaling pathways can enable scientists to better understand cell signaling in other developmental and disease processes. Identification of novel MAP kinases provides the opportunity to diagnose or intervene in such disease processes.

DISCLOSURE OF THE INVENTION

The subject invention provides a unique nucleotide sequence, herein designated in lower case, smap (SEQ ID NO:1) which encodes a novel human MAP kinase protein, designated in upper case, SMAP (SEQ ID NO:2). The cDNA encoding SMAP was identified and cloned using Incyte Clone No. 214915 from a stomach cDNA library.

The invention also relates to the use of the nucleotide and amino acid sequences of SMAP, or its variants, in the diagnosis and treatment of activated or inflamed cells and/or tissues associated with its expression. Aspects of the invention include the antisense DNA of smap; cloning or expression vectors containing smap; host cells transformed with the expression vector; a method for the production and recovery of purified SMAP from host cells; and purified protein, SMAP, which can be used to produce antibodies or identify inhibitors of the protein.

BRIEF DESCRIPTION OF DRAWINGS

FIGS. 1A, 1B and 1C display the alignment of the nucleotide sequence (SEQ ID NO:1) and amino acid sequence (SEQ ID NO:2) for human MAP kinase homolog produced using MacDNAsis software (Hitachi Software Engineering Co Ltd).

FIG. 2 shows the amino acid alignment between SMAP and mouse kinase, GenBank 531125 (locus MMU10871; Han et al. (1994) Science 265: 808–810).

FIG. 3 shows the amino acid alignment between SMAP and the closely related mitogen activated protein kinase homolog, GenBank 603917 (locus HUMCSBP1; Lee et al (1994) Nature 372: 739–746). Alignments for FIGS. 2 and 3 were produced using the INHERIT™ 670 Sequence Analysis System (Applied Biosystems, Foster City, Calif.).

MODES FOR CARRYING OUT THE INVENTION

Definitions

As used herein, the lowercase letters, "smap", refer to a gene, cDNA or nucleic acid sequence for the novel human MAP kinase homolog while the uppercase letters, "SMAP", refer to the protein sequence encoded by human MAP kinase homolog.

The present invention provides a unique nucleotide sequence identifying a novel MAP kinase homolog from human stomach cell, SEQ ID NO:1. The coding region of SEQ ID NO:1 begins at nucleotide 58 and ends at nucleotide 1156. Since SMAP is specifically involved with protective cell signaling processes, the nucleic acid, protein, and antibodies are useful in the study, diagnosis and treatment of conditions which affect the stomach such as gastritis, ulcers, viral and bacterial infections, neoplasms and the like.

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, confirm, or reveal the presence of smap DNA or RNA in a particular cell or tissue. Oligonucleotides or oligomers comprise portions of a DNA sequence having at least about 10 nucleotides and as many as about 50 nucleotides, preferably about 15 to 30 nucleotides.

"Probes" are nucleic acid sequences of variable length, preferably between 10 and 6,000 nucleotides, which may be chemically synthesized, naturally occurring, or recombinant single- or double-stranded nucleic acids. They are useful in the qualitative or quantitative detection of the same, a similar, or a complementary nucleic acid sequence.

"Reporter" molecules are chemical moieties used for labelling a nucleic or amino acid sequence. They include, but are not limited to, radionuclides, enzymes, fluorescent, chemi-luminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Recombinant nucleotide variants" are polynucleotides which encode SMAP. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Linkers" are synthesized palindromic oligomers which create internal restriction endonuclease sites.

"Chimeric" genes are polynucleotides which may be constructed by introducing all or part of the nucleotide sequence of this invention into a vector containing additional nucleic acid sequence(s). Such sequences may be expected to change any one (or more than one) of the following SMAP characteristics: cellular location, distribution, ligand-binding affinities, interchain affinities, degradation/turnover rate, signalling, etc.

"Active" refers to those forms, fragments, or domains of any SMAP polypeptide which display the biologic and/or immunogenic activities of any naturally occurring SMAP.

"Naturally occurring SMAP" refers to a polypeptide produced by cells which have not been genetically engineered and specifically contemplates various polypeptides which arise from post-translational modifications. Such modifications of the polypeptide include are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring SMAP by amino acid insertions, deletions and/or substitutions, created using recombinant DNA techniques. Guidance in determining which amino acid residues may be replaced, added or deleted without abolishing activities of interest may be found by comparing the sequence of SMAP with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the smap sequence using recombinant DNA techniques.

A "signal or leader sequence" is a short amino acid sequence which can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment," "portion," or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

An "inhibitor" is a substance which retards or prevents a chemical or physiological reaction or response. Common inhibitors include but are not limited to antisense molecules, antibodies, and antagonists.

A "standard" is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (cats, dogs, etc.), agricultural (cows, horses, sheep, etc.) or test species (mouse, rat, rabbit, etc.).

Kinase nucleotide sequences have numerous applications in techniques known to those skilled in the art of molecular biology. These techniques include the use of kinase sequences as hybridization probes, for chromosome and gene mapping, in the design of oligomers for PCR, and in the production of sense or antisense nucleic acids, their chemical analogs and the like. These examples are well known and are not intended to be limiting. Furthermore, the nucleotide sequences disclosed herein may be used in molecular biology techniques that have not yet been developed, provided the new techniques rely on properties of nucleotide sequences that are currently known such as the triplet genetic code, specific base pair interactions, etc.

As a result of the degeneracy of the genetic code, a multitude of kinase-encoding nucleotide sequences may be produced and some of these will bear only minimal homology to the endogenous sequence of any known and naturally occurring kinase. This invention has specifically contemplated each and every possible variation of nucleotide sequence that could be made by selecting combinations based on possible codon choices. These combinations are made in accordance with the standard triplet genetic code as applied to the nucleotide sequence of naturally occurring kinases, and all such variations are to be considered as being specifically disclosed.

Although the nucleotide sequences which encode a specific kinase and its derivatives or variants are preferably capable of identifying the nucleotide sequence of the naturally occurring kinase under optimized conditions, it may be advantageous to produce smap possessing a substantially different codon usage. Codons can be selected to increase the rate of peptide expression in a particular prokaryotic or eukaryotic expression host in accordance with the frequency with which particular codons are utilized by the host. Other reasons for substantially altering the nucleotide sequence encoding the kinase without altering the encoded amino acid sequence include the production of RNA transcripts having more desirable properties, such as a longer half-life, than transcripts produced from the naturally occurring sequence.

Nucleotide sequences encoding a kinase may be joined to a variety of other nucleotide sequences by means of well established recombinant DNA techniques (Sambrook, J. et al (1989) Molecular Cloning: A Laboratory Manual, Cold Spring Harbor Laboratory, Cold Spring Harbor, N.Y.; or Ausubel, F. M. et al (1989) Current Protocols in Molecular Biology, John Wiley & Sons, New York City). Useful nucleotide sequences for joining to the kinase include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

Another aspect of the subject invention provides for kinase hybridization probes which are capable of hybridizing with naturally occurring nucleotide sequences encoding kinases. The stringency of the hybridization conditions will determine whether the probe identifies only nucleotide sequence of that specific kinase or sequences of closely related molecules. If such probes are used for the detection of related kinase encoding sequences, they should preferably contain at least 50% of the nucleotides from any of the sequence presented here. Hybridization probes of the subject invention may be derived from the nucleotide sequences of the SEQ ID NO:1 or from an isolated genomic sequence including untranslated regions such as promoters, enhancers and introns. Such hybridization probes may be labeled with reporter molecules.

PCR as described in U.S. Pat. Nos. 4,683,195; 4,800,195; and 4,965,188 provides additional uses for oligonucleotides based upon the kinase nucleotide sequence. Such oligomers may be of recombinant origin, chemically synthesized, or a mixture of both. Oligomers may comprise two nucleotide sequences employed under optimized conditions for tissue specific identification or diagnostic use. The same two oligomers, nested sets of oligomers, or even a degenerate pool of oligomers may be employed under less stringent conditions for identification of closely related DNA or RNA sequences.

Full length genes may be cloned from known sequence using a new method disclosed in U.S. patent application Ser. No. 08/487,112 filed Jun. 7, 1995 and hereby incorporated by reference, which employs XL-PCR (Perkin-Elmer, Foster City, Calif.) to amplify long pieces of DNA. This method was developed to allow a single researcher to process multiple genes (up to 20 or more) at a time and to obtain an extended (possibly full-length) sequence within 6–10 days. It replaces current methods which use labeled probes to screen libraries and allow one researcher to process only about 3–5 genes in 14–40 days.

In the first step, which can be performed in about two days, primers are designed and synthesized based on a known partial sequence. In step 2, which takes about six to eight hours, the sequence is extended by PCR amplification of a selected library. Steps 3 and 4, which take about one day, are purification of the amplified cDNA and its ligation into an appropriate vector, respectively. Step 5, which takes about one day, involves transforming and growing up host bacteria. In step 6, which takes approximately five hours, PCR is used to screen bacterial clones for extended sequence. The final steps, which take about one day, involve the preparation and sequencing of selected clones. If the full length cDNA has not been obtained, the entire procedure is repeated using either the original library or some other preferred library. The preferred library may be one that has been size-selected to include only larger cDNAs or may consist of single or combined commercially available libraries, eg. lung, liver, heart and brain from Gibco/BRL (Gaithersburg, Md.). The cDNA library may have been prepared with oligo d(T) or random primers. The advantage of using random primed libraries is that they will have more sequences which contain 5' ends of genes. A randomly primed library may be particularly useful if an oligo d(T) library does not yield a complete gene. Obviously, the larger the protein, the less likely it is that the complete gene will be found in a single plasmid.

Other means of producing specific hybridization probes for kinases include the cloning of the cDNA sequences into vectors for the production of mRNA probes. Such vectors are known in the art, are commercially available, and may be used to synthesize RNA probes in vitro by addition of an appropriate RNA polymerase such as T7 or SP6 and labeled nucleotides.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with a portion of an existing genomic or recombinant sequence.

The kinase nucleotide sequences can be used individually, or in panels, in an assay to detect inflammation or disease associated with abnormal levels of kinase expression. The nucleotide sequence is added to a fluid, cell or tissue sample from a patient under hybridizing conditions. After an incubation period, the sample is washed with a compatible fluid which optionally contains a reporter molecule which will bind the specific nucleotide. After the compatible fluid is rinsed off, the reporter molecule is quantitated and compared with a standard for that fluid, cell or tissue. If kinase expression is significantly different from the standard, the assay indicates the presence of inflammation or disease.

This same assay, combining a sample with the nucleotide sequence, is applicable in evaluating the efficacy of a particular therapeutic treatment regime. It may be used in animal studies, in clinical trials, or in monitoring the treatment of an individual patient. First, standard expression must be established for use as a basis of comparison. Second, samples from the animals or patients affected by the disease are combined with the nucleotide sequence to evaluate the deviation from the standard or normal profile. Third, an existing therapeutic agent is administered, and a treatment profile is generated. The assay is evaluated to determine whether the profile progresses toward or returns to the standard pattern. Successive treatment profiles may be used to show the effects of treatment over a period of several days or over several months.

The cDNA for human MAP kinase can also be used to design hybridization probes for mapping the native genomic sequence. The sequence may be mapped to a particular chromosome or to a specific region of the chromosome using well known techniques. These include in situ hybridization to chromosomal spreads (Verma et al (1988) Human Chromosomes: A Manual of Basic Techniques, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic map data can be found in the 1994 Genome Issue of Science (265: 1981f). Often the placement of a gene on the chromosome of another mammalian species may reveal associated markers even if the number or arm of a particular human chromosome is not known. New nucleotide sequences can be assigned to chromosomal subregions by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336: 577–580), any sequences mapping to that area may represent genes for further investigation of AT. The nucleotide sequence of the subject invention may also be used to detect differences in gene sequence between normal and carrier or affected individuals.

Nucleotide sequences encoding a Particular kinase may be used to produce purified oligopeptide using well known methods of recombinant DNA technology. Goeddel (1990, Gene Expression Technology, Methods and Enzymology, Vol 185, Academic Press, San Diego, Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with a kinase nucleotide sequence may be cultured under conditions suitable for the expression and recovery of the oligopeptide from cell culture. The oligopeptide produced by a recombinant cell may be secreted or may be contained intracellularly depending on the sequence and the genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the kinase sequence to a nucleic acid sequence encoding a polypeptide domain which will facilitate protein purification (Kroll, D. J. et al (1993) DNA Cell Biol 12: 441–53).

In addition to recombinant or chimeric production, kinase fragments may be produced by direct peptide synthesis using solid-phase techniques (Stewart et al (1969) Solid-Phase Peptide Synthesis, W. H. Freeman Co, San Francisco, Calif.; Merrifield, J. (1963) J Am Chem Soc 85: 2149–2154). Automated synthesis may be achieved, for example, using Applied Biosystems 431A Peptide Synthesizer in accordance with the instructions provided by the manufacturer. Additionally a particular kinase sequence, or any part thereof, may be mutated during chemical synthesis, combined using chemical methods with other kinase sequence(s), and used in an appropriate vector and host cell to produce a polypeptide.

Although the amino acid sequence or oligopeptide used for antibody induction does not require biological activity, it must be antigenic and consist of at least five amino acids and preferably at least 10 amino acids. Short stretches of amino acid sequence may be fused with those of another protein such as keyhole limpet hemocyanin, and the chimeric peptide used for antibody production.

Antibodies specific for SMAP may be produced by inoculation of an appropriate animal with an antigenic fragment of the peptide. An antibody is specific for SMAP if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (Orlandi, R. et al (1989) PNAS 86: 3833–3837, or Huse, W. D. et al (1989) Science 256: 1275–1281), or the in vitro stimulation of lymphocyte populations. Current technology (Winter, G. and Milstein, C. (1991) Nature 349: 293–299) provides for a number of highly specific binding reagents based on the principles of antibody formation. These techniques may be adapted to produce molecules which specifically bind SMAPs.

The examples below are provided to illustrate the subject invention. These examples are provided by way of illustration and are not included for the purpose of limiting the invention.

INDUSTRIAL APPLICABILITY

I Isolation of mRNA and Construction of the cDNA Library

The partial cDNA sequence for the human MAP kinase homolog was initially identified in Incyte Clone 214915 among the sequences comprising the human stomach cell library, U.S. patent application Ser. No. 08/385,268, filed 7 Feb. 1995, disclosed herein by reference. The normal stomach tissue used for this library was obtained from the Keystone Skin Bank, International Institute for the Advancement of Medicine (Exton, Pa.).

Five grams of normal stomach tissue from a 55 year old male (KSP93-B72) was flash frozen, ground in a mortar and pestle, and lysed immediately in buffer containing guanidinium isothiocyanate. Lysis was followed by centrifugation through cesium chloride, incubation with DNase and ethanol precipitation.

The RNA was sent to Stratagene (La Jolla, Calif.) and oligo d(T) priming was used to prepare the cDNA library. Synthetic linkers were ligated onto the cDNA molecules, and they were inserted into the Uni-ZAP™ vector system (Stratagene).

II Isolation of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells, purified, and used to reinfect fresh host cells (SOLR, Stratagene) where double-stranded phagemid DNA was produced.

Phagemid DNA was purified using the QIAWELL-8™ Plasmid Purification System (QIAGEN Inc, Chatsworth, Calif.). This product lyses bacterial cells and allows the isolation of highly purified phagemid DNA using OIAGEN anion-exchange resin particles in a multiwell format. The DNA was eluted from the purification resin and prepared for DNA sequencing and other analytical manipulations.

An alternate method of purifying phagemid utilizes the Miniprep Kit (Catalog No. 77468; Advanced Genetic Technologies Corp, Gaithersburg, Md.). The kit has a 96-well format and provides enough reagents for 960 purifications. The recommended protocol is employed except for the following changes. First, each of the 96 wells is filled with 1 ml of sterile terrific broth (LIFE TECHNOLOGIES™, Gaithersburg, Md.) containing carbenicillin at 25 mg/L and glycerol at 0.4%. The bacteria are introduced into the wells, cultured for 24 hours and lysed with 60 μl of lysis buffer. The block is centrifuged at 2900 rpm for 5 minutes and then the contents of the block are added to the primary filter plate. An optional step of adding isopropanol to the TRIS buffer is not routinely performed. Following the last step in the protocol, samples are transferred to a Beckman 96-well block for storage.

III Sequencing of cDNA Clones

The cDNA inserts from random isolates of the stomach library were sequenced in part. Methods for DNA sequencing are well known in the art and employ such enzymes as SEQUENAS® (U.S. Biochemical Corp, Cleveland, Ohio) or Taq polymerase. Methods to extend the DNA from an oligonucleotide primer annealed to the DNA template of interest have been developed for the use of both single- and double-stranded templates. The chain termination reaction products were separated using electrophoresis and urea-acrylamide gels and detected either by autoradiography with radionuclide-labeled precursors or by fluorescent or chromogenic labelling. Recent improvements in mechanized reaction preparation, sequencing and analysis using the latter methods have permitted expansion in the number of sequences determined per day. The machines used in these processes include the Catalyst 800, Hamilton Micro Lab 2200 (Hamilton, Reno, Nev.), Peltier Thermal Cycler (PTC200; MJ Research, Watertown, Mass.) and the Applied Biosystems 377 and 373 DNA sequencers.

IV Homology Searching of cONA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul, S. F. (1993) J Mol Evol 36: 290–300; Altschul, S. F. et al (1990) J Mol Biol 215: 403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Extension of the cDNA to Full Length

Analysis of the INHERIT™ results from the randomly picked and sequenced portions of clones from the stomach library identified Incyte 214915 as a homolog of MAP kinase. The cDNA of Incyte 214915 was extended to full length using a modified XL-PCR (Perkin Elmer) procedure. Primers were designed based on the known sequence; one primer was synthesized to initiate extension in the antisense direction (XLR) and the other to extend sequence in the sense direction (XLF). The primers allowed the sequence to be extended "outward" generating amplicons containing new, unknown nucleotide sequence for the gene of interest. The primers were designed using Oligo 4.0 (National Biosciences Inc, Plymouth, Minn.) to be 22–30 nucleotides in length, to have a GC content of 50% or more, and to anneal to the target sequence at temperatures about 68°–72° C. Any stretch of nucleotides which would result in hairpin structures and primer-primer dimerizations was avoided.

The stomach cDNA library was used as a template, and XLR=MG ACA TCC AGG AGC CCA ATG AC and XLF= AGG TGA TCC TCA GCT GGA TGC AC primers were used to extend and amplify the 214915 sequence. By following the instructions for the XL-PCR kit and thoroughly mixing the enzyme and reaction mix, high fidelity amplification is obtained. Beginning with 25 pMol of each primer and the recommended concentrations of all other components of the kit, PCR was performed using the Peltier thermal cycler (MJ PTC200; MJ Research, Watertown, Mass.) and the following parameters:

Step 1 94° C. for 60 sec (initial denaturation)
Step 2 94° C. for 15 sec
Step 3 65° C. for 1 min
Step 4 68° C. for 7 min
Step 5 Repeat step 2–4 for 15 additional times
Step 6 94° C. for 15 sec
Step 7 65° C. for 1 min
Step 8 68° C. for 7 min+15 sec/cycle
Step 9 Repeat step 6–8 for 11 additional times
Step 10 72° C for 8 min
Step 11 4° C. (and holding)

At the end of 28 cycles, 50 µl of the reaction mix was removed; and the remaining reaction mix was run for an additional 10 cycles as outlined below:

Step 1 94° C. for 15 sec
Step 2 65° C. for 1 min
Step 3 68° C. for (10 min+15 sec)/cycle
Step 4 Repeat step 1–3 for 9 additional times
Step 5 72° C. for 10 min A 5–10 µl aliquot of the reaction mixture was analyzed by electrophoresis on a low concentration (about 0.6–0.8%) agarose mini-gel to determine which reactions were successful in extending the sequence. Although all extensions potentially contain a full length gene, some of the largest products or bands were selected and cut out of the gel. Further purification involved using a commercial gel extraction method such as QIAQuick™ (QIAGEN Inc). After recovery of the DNA, Klenow enzyme was used to trim single-stranded, nucleotide overhangs creating blunt ends which facilitated religation and cloning.

After ethanol precipitation, the products were redissolved in 13 µl of ligation buffer. Then, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook, J. et al, supra). After incubation for one hour at 37° C., the whole transformation mixture was plated on Luria Bertani (LB)-agar (Sambrook, J. et al, supra) containing carbenicillin at 25 mg/L. The following day, 12 colonies were randomly picked from each plate and cultured in 150 µl of liquid LB/carbenicillin medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 15 µl of concentrated PCR reaction mix (1.33×) containing 0.75 units of Taq polymerase, a vector primer and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 times
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid and sequenced.

When the three possible amino acid translations of the full length cDNA sequence were searched against protein databases such as SwissProt and PIR, no exact matches were found. FIG. 1 shows the nucleotide and amino acid sequences for human MAP kinase homolog. The alignment of the amino acid sequence for SMAP (SEQ ID NO: 2) with MMU10871 (GI 531125, SEQ ID NO:3) and HUMCSBP1 (GI 603917) are shown in FIGS. 2 and 3, respectively.

VI Sense or Antisense Molecules

Knowledge of the correct cDNA sequence of any particular kinase, or part thereof, enables its use as a tool in sense or antisense technologies for the investigation of gene function. Oligonucleotides, from genomic or cDNAs, comprising either the sense or the antisense strand of the cDNA sequence is used in vitro or in vivo to inhibit expression. Such technology is now well known in the art, and oligonucleotides or other fragments are designed from various locations along the sequences. The gene of interest is turned off in the short term by transfecting a cell or tissue with expression vectors which flood the cell with sense or antisense sequences until all copies of the vector are disabled by endogenous nucleases. Stable transfection of appropriate germ line cells or a zygote with a vector containing the fragment produces a transgenic organism (U.S. Pat. No. 4,736,866, 12 Apr. 1988), whose cells produce enough copies of the sense or antisense sequence to significantly compromise or entirely eliminate normal activity of the particular kinase gene. Frequently, the function of the gene is ascertained by observing behaviors such as lethality, loss of a physiological pathway, changes in morphology, etc. at the intracellular, cellular, tissue or organismal level.

In addition to using fragments constructed to- interrupt transcription of the open reading frame, modifications of gene expression are obtained by designing antisense sequences to promoters, enhancers, introns, or even to transacting regulatory genes. Similarly, inhibition is achieved using Hogeboom base-pairing methodology, also known as "triple helix" base pairing.

VII Expression of SMAP

Expression of smap is accomplished by subcloning the cDNAs into appropriate expression vectors and transfecting the vectors into an appropriate expression hosts. In this particular case, the cloning vector previously used for the generation of the tissue library also provide for direct expression of smap sequences in *E. coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods produces a fusion protein corresponding to the first seven residues of β-galactosidase, about 5 to 15 residues which correspond to linker, and the peptide encoded within the cDNA. Since cDNA clone inserts are generated by an essentially random process, there is one chance in three that the included cDNA lies in the correct frame for proper translation. If the cDNA is not in the proper reading frame, it is obtained by deletion or insertion of the appropriate number of bases by well known methods including in vitro mutagenesis, digestion with exonuclease III or mung bean nuclease, or oligonucleotide linker inclusion.

The smap cDNA is shuttled into other vectors known to be useful for expression of protein in specific hosts. Oligonucleotide linkers containing cloning sites as well as a segment of DNA sufficient to hybridize to stretches at both ends of the target cDNA (25 bases) is synthesized chemically by standard methods. These primers are then used to amplify the desired gene segments by PCR. The resulting new gene segments are digested with appropriate restriction enzymes under standard conditions and isolated by gel electrophoresis. Alternately, similar gene segments are produced by digestion of the CDNA with appropriate restriction enzymes and filling in the missing gene segments with chemically synthesized oligonucleotides. Segments of the coding sequence from more than one gene are ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae,* and bacteria such as *E. coli.* For each of these cell systems, a useful expression vector includes an origin of replication to allow propagation in bacteria and a selectable marker such as the β-lactamase antibiotic resistance gene to allow selection in bacteria. In addition, the vectors include a second selectable marker such as the neomycin phosphotransferase gene to allow selection in transfected eukaryotic host cells. Vectors for use in eukaryotic expression hosts usually require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus (RSV) enhancer, is used in mammalian host cells. Once homogeneous cultures of recombinant cells are obtained through standard culture methods, large quantities of recombinantly produced SMAP are recovered from the conditioned medium and analyzed using chromatographic methods known in the art.

VIII Isolation of Recombinant SMAP

SMAP is expressed as a chimeric protein with one or more additional polypeptide domains added to facilitate protein purification. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle. Wash.). The inclusion of a cleavable linker sequence such as Factor XA or enterokinase (Invitrogen) between the purification domain and the smap sequence is useful to facilitate purification of SMAP.

IX Production of SMAP Specific Antibodies

Two approaches are utilized to raise antibodies to SMAP, and each approach is useful for generating either polyclonal or monoclonal antibodies. In one approach, denatured protein from the reverse phase HPLC separation is obtained in quantities up to 75 mg. This denatured protein is used to immunize mice or rabbits using standard protocols; about 100 micrograms are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of SMAP, as deduced from translation of the cDNA, is analyzed to determine regions of high immunogenicity. Oligopeptides comprising appropriate hydrophilic regions are synthesized and used in suitable immunization protocols to raise antibodies. Analysis to select appropriate epitopes is described by Ausubel, F. M. et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; Ausubel, F. M. et al, supra). If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled SMAP to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable anti-species Ig) antibodies at 10 mg/ml. The coated wells are blocked with 1% BSA, washed and incubated with supernatants from hybridomas. After washing the wells are incubated with labeled SMAP at 1 mg/ml. Supernatants with specific antibodies bind more labeled SMAP than is detectable in the background. Then clones producing specific antibodies are expanded and subjected to two cycles of cloning at limiting dilution (1 cell/3 wells). Cloned hybridomas are injected into pristane-treated mice to produce ascites, and monoclonal antibody is purified from mouse ascitic fluid by affinity chromatography on Protein A. Monoclonal antibodies with affinities of at least $10^8$/M, preferably $10^9$ to $10^{10}$ or stronger, are typically made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

X Diagnostic Test Using SMAP Specific Antibodies

Particular SMAP antibodies are useful for investigation of various forms of stomach conditions characterized by differences in the amount or distribution of SMAP. Given the usual role of MAP kinases, SMAP from the human stomach library appears to be upregulated in its characteristic involvement in immune protection or defense.

Diagnostic tests for SMAP include methods utilizing the antibody and a label to detect SMAP in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins are produced as shown in U.S. Pat. No. 4,816,567, incorporated herein by reference.

A variety of protocols for measuring soluble or membrane-bound SMAP, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on SMAP is preferred, but a competitive binding assay may be employed. These assays are described, among other places, in Maddox, D. E. et al (1983, J Exp Med 158: 1211).

XI Purification of Native SMAP Using Specific Antibodies

Native or recombinant SMAP is purified by immunoaffinity chromatography using antibodies specific for SMAP. In general, an immunoaffinity column is constructed by covalently coupling the anti-SMAP antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of SMAP by preparing a fraction from cells containing SMAP in a soluble form. This preparation is derived by solubilization of whole cells or of a subcellular fraction obtained via differential centrifugation (with or without addition of detergent) or by other methods well known in the art. Alternatively, soluble SMAP containing a signal sequence is secreted in useful quantity into the medium in which the cells are grown.

A soluble SMAP-containing preparation is passed over the immunoaffinity column, and the column is washed under conditions that allow the preferential absorbance of SMAP (eg, high ionic strength buffers in the presence of detergent). Then, the column is eluted under conditions that disrupt antibody/SMAP binding (eg, a buffer of pH 2–3 or a high concentration of a chaotrope such as urea or thiocyanate ion), and SMAP is collected.

XII Drug Screening

This invention is particularly useful for screening therapeutic compounds by using SMAP or binding fragments thereof in any of a variety of drug screening techniques. The polypeptide or fragment employed in such a test is either free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, are used for standard binding assays. One measures, for example, the formation of complexes between SMAP and the agent being tested. Alternatively, one can examine the diminution in complex formation between SMAP and a receptor caused by the agent being tested.

Thus, the present invention provides methods of screening for drugs or any other agents which affect signal transduction. These methods comprise contacting such an agent with SMAP polypeptide or a fragment thereof and assaying (i) for the presence of a complex between the agent and the SMAP polypeptide or fragment, or (ii) for the presence of a complex between the SMAP polypeptide or fragment and the cell, by methods well known in the art. In such competitive binding assays, the SMAP polypeptide or fragment is typically labeled. After suitable incubation, free SMAP polypeptide or fragment is separated from that present in bound form, and the amount of free or uncomplexed label is a measure of the ability of the particular agent to bind to SMAP or to interfere with the SMAP and agent complex.

Another technique for drug screening provides high throughput screening for compounds having suitable binding affinity to the SMAP polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with SMAP polypeptide and washed. Bound SMAP polypeptide is then detected by methods well known in the art. Purified SMAP may also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding SMAP specifically compete with a test compound for binding to SMAP polypeptides or fragments thereof. In this manner, the antibodies are used to detect the presence of any peptide which shares one or more antigenic determinants with SMAP.

XIII Rational Drug Design

The goal of rational drug design is to produce structural analogs of biologically active polypeptides of interest or of small molecules with which they interact, e.g., agonists, antagonists, or inhibitors. Any of these examples are used to fashion drugs which are more active or stable forms of the polypeptide or which enhance or interfere with the function of a polypeptide in vivo (Hodgson, J. (1991) Bio/Technology 9: 19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design include molecules which have improved activity or stability as shown by Braxton, S. and Wells, J. A. (1992 Biochemistry 31: 7796–7801) or which act as inhibitors, agonists, or antagonists of native peptides as shown by Athauda, S. B. et al (1993 J Biochem 113: 742–746), incorporated herein by reference.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id is then used to identify and isolate peptides from banks of chemically or biologically produced peptides. The isolated peptides then act as the pharmacore.

By virtue of the present invention, sufficient amount of polypeptide is made available to perform such analytical studies as X-ray crystallography. In addition, knowledge of the SMAP amino acid sequence provided herein provides guidance to those employing computer modeling techniques in place of or in addition to x-ray crystallography.

XIV Identification of Other Members of the Signal Transduction Complex

The inventive purified SMAP is a research tool for identification, characterization and purification of interacting or signal transduction pathway proteins. Radioactive labels are incorporated into SMAP by various methods known in the art and used to capture either soluble or membrane-bound molecules. A preferred method involves labeling the primary amino groups in SMAP with $^{125}$I Bolton-Hunter reagent (Bolton, A. E. and Hunter, W. M. (1973) Biochem J 133: 529). This reagent has been used to label various molecules without concomitant loss of biological activity (Hebert, C. A. et al (1991) J Biol Chem 266: 18989; McColl, S. et al (1993) J Immunol 150: 4550–4555). Membrane-bound molecules are incubated with the labeled SMAP molecules, washed to removed unbound molecules, and the SMAP complex is quantified. Data obtained using different concentrations of SMAP are used to calculate values for the number, affinity, and association of SMAP complex.

Labeled SMAP is also useful as a reagent for the purification of molecules with which SMAP interacts. In one embodiment of affinity purification, SMAP is covalently coupled to a chromatography column. Cells and their membranes are extracted, SMAP is removed and various SMAP-free subcomponents are passed over the column. Molecules bind to the column by virtue of their SMAP affinity. The SMAP-complex is recovered from the column, dissociated and the recovered molecule is subjected to N-terminal protein sequencing. This amino acid sequence is then used to identify the captured molecule or to design degenerate oligonucleotide probes for cloning its gene from an appropriate cDNA library.

In another alternate method, antibodies are raised against SMAP, specifically monoclonal antibodies. The monoclonal antibodies are screened to identify those which inhibit the binding of labeled SMAP. These monoclonal antibodies are then used in affinity purification or expression cloning of associated molecules.

Other soluble binding molecules are identified in a similar manner. Labeled SMAP is incubated with extracts or other appropriate materials derived from stomach or other gastrointestinal mucosa. After incubation, SMAP complexes (which are larger than the lone SMAP molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XV Use and Administration of Antibodies, Inhibitors, Receptors or Antagonists of SMAP Antibodies, inhibitors, receptors or antagonists of SMAP (or other treatments to limit signal transduction, TST) provide different effects when administered therapeutically. TSTs are formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TSTs include solubility of the molecule, half-life and antigenicity/immunogenicity; these and other characteristics aid in defining an effective carrier. Native human proteins are preferred as TSTs, but organic or synthetic molecules resulting from drug screens are equally effective in particular situations.

TSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration are determined by the attending physician and vary according to each specific situation.

Such determinations are made by considering multiple variables such as the condition to be treated, the TST to be administered, and the pharmacokinetic profile of the particular TST. Additional factors which are taken into account include disease state (e.g. severity) of the patient, age, weight, gender, diet, time and frequency of administration, drug combination, reaction sensitivities, and tolerance/response to therapy. Long acting TST formulations might be administered every 3 to 4 days, every week, or once every two weeks depending on half-life and clearance rate of the particular TST.

Normal dosage amounts vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art employ different formulations for different TSTs. Administration to cells such as nerve cells necessitates delivery in a manner different from that to other cells such as vascular endothelial cells.

It is contemplated that conditions or diseases-which trigger defensive signal transduction may precipitate damage that is treatable with TSTs. These conditions or diseases are specifically diagnosed by the tests discussed above, and such testing should be performed in suspected cases of stomach conditions such as gastritis, ulcers, viral and bacterial infections, or neoplasms associated with abnormal signal transduction.

All publications and patents mentioned in the above specification are herein incorporated by reference. Various modifications and variations of the described method and system of the invention are apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. A method for producing a polypeptide comprising the amino acid sequence of SEQ ID NO:2, the method comprising the steps of:

a) culturing a host cell transformed with a vector comprising a polynucleotide encoding SEQ ID NO:2 under conditions suitable for the expression of the polypeptide; and b) recovering the polypeptide from the host cell culture.

2. A purified polypeptide comprising the amino acid sequence of SEQ ID NO:2.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1851 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Stomach
        ( B ) CLONE: 214915

( x i ) SEQUENCE DESCRIPTION: SEQ ID NO:1:

| | | | | | | |
|---|---|---|---|---|---|---|
| GCCCGTTGGG | CCGCGAACGC | AGCCGCCACG | CCGGGGCCGC | CGAGATCGGG | TGCCCGGGAT | 60 |
| GAGCCTCATC | CGGAAAAAGG | GCTTCTACAA | GCAGGACGTC | AACAAGACCG | CCTGGGAGCT | 120 |
| GCCCAAGACC | TACGTGTCCC | CGACGCACGT | CGGCAGCGGG | GCCTATGGCT | CCGTGTGCTC | 180 |
| GGCCATCGAC | AAGCGGTCAG | GGGAGAAGGT | GGCCATCAAG | AAGCTGAGCC | GACCCTTTCA | 240 |
| GTCCGAGATC | TTCGCCAAGC | GCGCCTACCG | GGAGCTGCTG | TTGCTGAAGC | ACATGCAGCA | 300 |
| TGAGAACGTC | ATTGGGCTCC | TGGATGTCTT | CACCCCAGCC | TCCTCCCTGG | AACTTCTATG | 360 |
| ACTTCTACCT | GGTGATGCCC | TTCATGCAGA | CGGATCTGCA | GAAGATCATG | GGGATGGAGT | 420 |
| TCAGTGAGGA | GAAGATCCAG | TACCTGGTGT | ATCAGATGCT | CAAAGGCCTT | AAGTACATCC | 480 |

-continued

```
ACTCTGCTGG GGTCGTGCAC AGGGACCTGA AGCCAGGCAA CCTGGCTGTG AATGAGGACT      540
GTGAACTGAA GATTCTGGAT TTGGGGCTGG CGCGACATGC AGACGCCGAG ATGACTGGCT      600
ACGTGGTGAC CCGCTGGTAC CGAGCCCCCG AGGTGATCCT CAGCTGGATG CACTACAACC      660
AGACAGTGGA CATCTGGTCT GTGGGCTGTA TCATGGCAGA GATGCTGACA GGGAAAACTC      720
TGTTCAAGGG GAAAGATTAC CTGGACCAGC TGACCCAGAT CCTGAAAGTG ACCGGGGTGC      780
CTGGCACGGA GTTTGTGCAG AAGCTGAACG ACAAAGCGGC CAAATCCTAC ATCCAGTCCC      840
TGCCACAGAC CCCCAGGAAG GATTTCACTC AGCTGTTCCC ACGGGCCAGC CCCCAGCCTG      900
CGGACCTGCT GGAGAAGATG CTGGAGCTAG ACGTGGACAA GCGCCTGACG GCCGCGCAGG      960
CCCTCACCCA TCCCTTCTTT GAACCCTTCC GGGACCCTGA GGAAGAGACG GAGGCCCAGC     1020
AGCCGTTTGA TGATTCCTTA GAACACGAGA AACTCACAGT GGATGAATGG AAGCAGCACA     1080
TCTACAAGGA GATTGTGAAC TTCAGCCCCA TTGCCCGGAA GGACTCACGG CGCCGGAGTG     1140
GCATGAAGCT GTAGGGACTC ATCTTGCATG GCACCGCCGG CCAGACACTG CCCAAGGACC     1200
AGTATTTGTC ACTACCAAAC TCAGCCCTTC TTGGAATACA GCCTTTCAAG CAGAGGACAG     1260
AAGGGTCCTT CTCCTTATGT GGGAAATGGG CCTAGTAGAT GCAGAATTCA AAGATGTCGG     1320
TTGGGAGAAA CTAGCTCTGA TCCTAACAGG CCACGTTAAA CTGCCCATCT GGAGAATCGC     1380
CTGCAGGTGG GGCCCTTTCC TTCCCGCCAG AGTGGGGCTG AGTGGGCGCT GAGCCAGGCC     1440
GGGGGCCTAT GGCAGTGATG CTGTGTTGGT TTCCTAGGGA TGCTCTAACG AATTACCACA     1500
AACCTGGTGG ATTGAAACAG CAGAACTTGA TTCCCTTACA GTTCTGGAGG CTGGAAATCT     1560
GGGATGGAGG TGTTGGCAGG GCTGTGGTCC CTTTGAAGGC TCTGGGGAAG AATCCTTCCT     1620
TGGCTCTTTT TAGCTTGTGG CGGCAGTGGG CAGTCCGTGG CATTCCCCAG CTTATTGCTG     1680
CATCACTCCA GTCTCTGTCT CTTCTGTTCT CTCCTCTTTT AACAACAGTC ATTGGATTTA     1740
GGGCCCACCC TAATCCTGTG TGATCTTATC TTGATCCTTA TTAATTAAAC CTGCAAATAC     1800
TCTAGTTCCA AATAAAGTCA CATTCTCAGG TAAAAAAAAA AAAAAAAAA A              1851
```

( 2 ) INFORMATION FOR SEQ ID NO:2:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( v i i ) IMMEDIATE SOURCE:
        ( A ) LIBRARY: Stomach
        ( B ) CLONE: 214915

( x i ) SEQUENCE DESCRIPTION: SEQ ID NO:2:

```
Met  Ser  Leu  Ile  Arg  Lys  Lys  Gly  Phe  Tyr  Lys  Gln  Asp  Val  Asn  Lys
  1                  5                        10                       15

Thr  Ala  Trp  Glu  Leu  Pro  Lys  Thr  Tyr  Val  Ser  Pro  Thr  His  Val  Gly
                20                       25                       30

Ser  Gly  Ala  Tyr  Gly  Ser  Val  Cys  Ser  Ala  Ile  Asp  Lys  Arg  Ser  Gly
            35                       40                       45

Glu  Lys  Val  Ala  Ile  Lys  Lys  Leu  Ser  Arg  Pro  Phe  Gln  Ser  Glu  Ile
       50                       55                       60

Phe  Ala  Lys  Arg  Ala  Tyr  Arg  Glu  Leu  Leu  Leu  Leu  Lys  His  Met  Gln
 65                      70                       75                       80

His  Glu  Asn  Val  Ile  Gly  Leu  Leu  Asp  Val  Phe  Thr  Pro  Ala  Ser  Ser
                     85                       90                       95
```

```
Leu Gly Asn Phe Tyr Asp Phe Tyr Leu Val Met Pro Phe Met Gln Thr
            100                 105                 110
Asp Leu Gln Lys Ile Met Gly Met Glu Phe Ser Glu Glu Lys Ile Gln
            115                 120                 125
Tyr Leu Val Tyr Gln Met Leu Lys Gly Leu Lys Tyr Ile His Ser Ala
            130                 135                 140
Gly Val Val His Arg Asp Leu Lys Pro Gly Asn Leu Ala Val Asn Glu
145                         150                 155                 160
Asp Cys Glu Leu Lys Ile Leu Asp Leu Gly Leu Ala Arg His Ala Asp
                    165                 170                 175
Ala Glu Met Thr Gly Tyr Val Val Thr Arg Trp Tyr Arg Ala Pro Glu
                180                 185                 190
Val Ile Leu Ser Trp Met His Tyr Asn Gln Thr Val Asp Ile Trp Ser
            195                 200                 205
Val Gly Cys Ile Met Ala Glu Met Leu Thr Gly Lys Thr Leu Phe Lys
            210                 215                 220
Gly Lys Asp Tyr Leu Asp Gln Leu Thr Gln Ile Leu Lys Val Thr Gly
225                         230                 235                 240
Val Pro Gly Thr Glu Phe Val Gln Lys Leu Asn Asp Lys Ala Ala Lys
                245                 250                 255
Ser Tyr Ile Gln Ser Leu Pro Gln Thr Pro Arg Lys Asp Phe Thr Gln
                260                 265                 270
Leu Phe Pro Arg Ala Ser Pro Gln Pro Ala Asp Leu Leu Glu Lys Met
            275                 280                 285
Leu Glu Leu Asp Val Asp Lys Arg Leu Thr Ala Ala Gln Ala Leu Thr
            290                 295                 300
His Pro Phe Phe Glu Pro Phe Arg Asp Pro Glu Glu Thr Glu Ala
305                 310                 315                 320
Gln Gln Pro Phe Asp Asp Ser Leu Glu His Glu Lys Leu Thr Val Asp
                325                 330                 335
Glu Trp Lys Gln His Ile Tyr Lys Glu Ile Val Asn Phe Ser Pro Ile
                340                 345                 350
Ala Arg Lys Asp Ser Arg Arg Arg Ser Gly Met Lys Leu
            355                 360                 365
```

( 2 ) INFORMATION FOR SEQ ID NO:3:

( i ) SEQUENCE CHARACTERISTICS:
        ( A ) LENGTH: 360 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:GenBank
        ( B ) CLONE: GI 531125

( x i ) SEQUENCE DESCRIPTION: SEQ ID NO:3:

```
Met Ser Gln Glu Arg Pro Thr Phe Tyr Arg Gln Glu Leu Asn Lys Thr
1               5                   10                  15
Ile Trp Glu Val Pro Glu Arg Tyr Gln Asn Leu Ser Pro Val Gly Ser
                20                  25                  30
Gly Ala Tyr Gly Ser Val Cys Ala Ala Phe Asp Thr Lys Thr Gly His
            35                  40                  45
Arg Val Ala Val Lys Lys Leu Ser Arg Pro Phe Gln Ser Ile Ile His
        50                  55                  60
```

| | | | | | | | | | | | | | | | |
|---|---|---|---|---|---|---|---|---|---|---|---|---|---|---|---|
| Ala | Lys | Arg | Thr | Tyr | Arg | Glu | Leu | Arg | Leu | Leu | Lys | His | Met | Lys | His |
| 65 | | | | | 70 | | | | 75 | | | | | | 80 |
| Glu | Asn | Val | Ile | Gly | Leu | Leu | Asp | Val | Phe | Thr | Pro | Ala | Arg | Ser | Leu |
| | | | | 85 | | | | | 90 | | | | | 95 | |
| Glu | Glu | Phe | Asn | Asp | Val | Tyr | Leu | Val | Thr | His | Leu | Met | Gly | Ala | Asp |
| | | | 100 | | | | | 105 | | | | | 110 | | |
| Leu | Asn | Asn | Ile | Val | Lys | Cys | Gln | Lys | Leu | Thr | Asp | Asp | His | Val | Gln |
| | | 115 | | | | | 120 | | | | | 125 | | | |
| Phe | Leu | Ile | Tyr | Gln | Ile | Leu | Arg | Gly | Leu | Lys | Tyr | Ile | His | Ser | Ala |
| | 130 | | | | | 135 | | | | | 140 | | | | |
| Asp | Ile | Ile | His | Arg | Asp | Leu | Lys | Pro | Ser | Asn | Leu | Ala | Val | Asn | Glu |
| 145 | | | | | 150 | | | | 155 | | | | | | 160 |
| Asp | Cys | Glu | Leu | Lys | Ile | Leu | Asp | Phe | Gly | Leu | Ala | Arg | His | Thr | Asp |
| | | | | 165 | | | | | 170 | | | | | 175 | |
| Asp | Glu | Met | Thr | Gly | Tyr | Val | Ala | Thr | Arg | Trp | Tyr | Arg | Ala | Pro | Glu |
| | | | 180 | | | | | 185 | | | | | 190 | | |
| Ile | Met | Leu | Asn | Trp | Met | His | Tyr | Asn | Gln | Thr | Val | Asp | Ile | Trp | Ser |
| | | 195 | | | | | 200 | | | | | 205 | | | |
| Val | Gly | Cys | Ile | Met | Ala | Glu | Leu | Leu | Thr | Gly | Arg | Thr | Leu | Phe | Pro |
| | 210 | | | | | 215 | | | | | 220 | | | | |
| Gly | Thr | Asp | His | Ile | Asp | Gln | Leu | Lys | Leu | Ile | Leu | Arg | Leu | Val | Gly |
| 225 | | | | | 230 | | | | 235 | | | | | | 240 |
| Thr | Pro | Gly | Ala | Glu | Leu | Leu | Lys | Lys | Ile | Ser | Ser | Glu | Ser | Ala | Arg |
| | | | | 245 | | | | | 250 | | | | | 255 | |
| Asn | Tyr | Ile | Gln | Ser | Leu | Ala | Gln | Met | Pro | Lys | Met | Asn | Phe | Ala | Asn |
| | | | 260 | | | | | 265 | | | | | 270 | | |
| Val | Phe | Ile | Gly | Ala | Asn | Pro | Leu | Ala | Val | Asp | Leu | Leu | Glu | Lys | Met |
| | | 275 | | | | | 280 | | | | | 285 | | | |
| Leu | Val | Leu | Asp | Ser | Asp | Lys | Arg | Ile | Thr | Ala | Ala | Gln | Ala | Leu | Ala |
| | 290 | | | | | 295 | | | | | 300 | | | | |
| His | Ala | Tyr | Phe | Ala | Gln | Tyr | His | Asp | Pro | Asp | Asp | Glu | Pro | Val | Ala |
| 305 | | | | | 310 | | | | 315 | | | | | | 320 |
| Asp | Pro | Tyr | Asp | Gln | Ser | Phe | Glu | Ser | Arg | Asp | Leu | Leu | Ile | Asp | Glu |
| | | | | 325 | | | | | 330 | | | | | 335 | |
| Trp | Lys | Ser | Leu | Thr | Tyr | Asp | Glu | Val | Ile | Ser | Phe | Val | Pro | Pro | Pro |
| | | | 340 | | | | | 345 | | | | | 350 | | |
| Leu | Asp | Gln | Glu | Glu | Met | Glu | Ser | | | | | | | | |
| | | 355 | | | | | 360 | | | | | | | | |

( 2 ) INFORMATION FOR SEQ ID NO:4:

( i ) SEQUENCE CHARACTERISTICS:
        ( A ) LENGTH: 360 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: Oligomer R
        ( B ) CLONE:

( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ser | Gln | Glu | Arg | Pro | Thr | Phe | Tyr | Arg | Gln | Glu | Leu | Asn | Lys | Thr |
| 1 | | | | 5 | | | | | 10 | | | | | 15 | |
| Ile | Trp | Glu | Val | Pro | Glu | Arg | Tyr | Gln | Asn | Leu | Ser | Pro | Val | Gly | Ser |
| | | | 20 | | | | | 25 | | | | | 30 | | |

| | | | | | | | | | | | | | | |
|---|---|---|---|---|---|---|---|---|---|---|---|---|---|---|
|Gly|Ala|Tyr 35|Gly|Ser|Val|Cys|Ala 40|Ala|Phe|Asp|Thr|Lys 45|Thr|Gly|Leu|
|Arg|Val 50|Ala|Val|Lys|Lys|Leu 55|Ser|Arg|Pro|Phe|Gln 60|Ser|Ile|Ile|His|
|Ala 65|Lys|Arg|Thr|Tyr 70|Arg|Glu|Leu|Arg|Leu 75|Leu|Lys|His|Met|Lys|His 80|
|Glu|Asn|Val|Ile|Gly 85|Leu|Leu|Asp|Val|Phe 90|Thr|Pro|Ala|Arg|Ser 95|Leu|
|Glu|Glu|Phe|Asn 100|Asp|Val|Tyr|Leu|Val 105|Thr|His|Leu|Met|Gly 110|Ala|Asp|
|Leu|Asn|Asn 115|Ile|Val|Lys|Cys|Gln 120|Lys|Leu|Thr|Asp|Asp 125|His|Val|Gln|
|Phe|Leu 130|Ile|Tyr|Gln|Ile|Leu 135|Arg|Gly|Leu|Lys|Tyr 140|Ile|His|Ser|Ala|
|Asp 145|Ile|Ile|His|Arg|Asp 150|Leu|Lys|Pro|Ser|Asn 155|Leu|Ala|Val|Asn|Glu 160|
|Asp|Cys|Glu|Leu|Lys 165|Ile|Leu|Asp|Phe|Gly 170|Leu|Ala|Arg|His|Thr 175|Asp|
|Asp|Glu|Met|Thr 180|Gly|Tyr|Val|Ala|Thr 185|Arg|Trp|Tyr|Arg|Ala 190|Pro|Glu|
|Ile|Met|Leu 195|Asn|Trp|Met|His|Tyr 200|Asn|Gln|Thr|Val|Asp 205|Ile|Trp|Ser|
|Val|Gly 210|Cys|Ile|Met|Ala|Glu 215|Leu|Leu|Thr|Gly|Arg 220|Thr|Leu|Phe|Pro|
|Gly 225|Thr|Asp|His|Ile|Asn 230|Gln|Leu|Gln|Gln|Ile 235|Met|Arg|Leu|Thr|Gly 240|
|Thr|Pro|Pro|Ala|Tyr 245|Leu|Ile|Asn|Arg|Met 250|Pro|Ser|His|Glu|Ala 255|Arg|
|Asn|Tyr|Ile|Gln 260|Ser|Leu|Thr|Gln|Met 265|Pro|Lys|Met|Asn|Phe 270|Ala|Asn|
|Val|Phe|Ile 275|Gly|Ala|Asn|Pro|Leu 280|Ala|Val|Asp|Leu|Leu 285|Glu|Lys|Met|
|Leu|Val 290|Leu|Asp|Ser|Asp|Lys 295|Arg|Ile|Thr|Ala|Ala 300|Gln|Ala|Leu|Ala|
|His 305|Ala|Tyr|Phe|Ala|Gln 310|Tyr|His|Asp|Pro|Asp 315|Asp|Glu|Pro|Val|Ala 320|
|Asp|Pro|Tyr|Asp|Gln 325|Ser|Phe|Glu|Ser|Arg 330|Asp|Leu|Leu|Ile|Asp 335|Glu|
|Trp|Lys|Ser|Leu 340|Thr|Tyr|Asp|Glu|Val 345|Ile|Ser|Phe|Val|Pro 350|Pro|Pro|
|Leu|Asp|Gln 355|Glu|Glu|Met|Glu|Ser 360| | | | | | | | |

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: Oligomer F
        ( B ) CLONE:

( x i ) SEQUENCE DESCRIPTION: SEQ ID NO:5:

AAGACATCCA GGAGCCCAAT G                                           21

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: GenBank
        ( B ) CLONE: GI 603917

( x i ) SEQUENCE DESCRIPTION: SEQ ID NO:6:

AGGTGATCCT CAGCTGGATG CAC                                         23